United States Patent [19]

Ramachandran

[11] Patent Number: 4,526,975

[45] Date of Patent: Jul. 2, 1985

[54] 2-AMINO-4-(4-PYRIDINYL)BENZOIC ACIDS

[75] Inventor: Venkataraman Ramachandran, Baton Rouge, La.

[73] Assignee: Ethyl Corporation, Richmond, Va.

[21] Appl. No.: 511,854

[22] Filed: Jul. 8, 1983

[51] Int. Cl.$^3$ .................. C07D 211/70; C07D 215/16
[52] U.S. Cl. ..................... 546/335; 546/156; 546/296; 546/300
[58] Field of Search ............... 546/296, 300, 335, 156

[56] References Cited

U.S. PATENT DOCUMENTS

| | | | |
|---|---|---|---|
| 3,753,993 | 8/1973 | Lesher et al. | 260/287 |
| 3,907,808 | 9/1975 | Lesher et al. | 260/287 |
| 4,118,557 | 10/1978 | Lesher | 542/420 |
| 4,398,029 | 8/1983 | Irikura et al. | 546/156 |

OTHER PUBLICATIONS

Mitscher et al., J. Med. Chem. 1978, vol. 21, No. 5, pp. 485–489.

*Primary Examiner*—Donald G. Daus
*Assistant Examiner*—Cecilia Shen
*Attorney, Agent, or Firm*—Donald L. Johnson; John F. Sieberth; Patricia J. Hogan

[57] ABSTRACT

2-Amino-4-(4-pyridinyl)benzoic acids, such as 2-amino-4-(4-pyridinyl)benzoic acid, are prepared by treating the appropriate 4-(4-alkyl-3-nitrophenyl)pyridine with an alcoholic base, such as methanolic potassium hydroxide. The products are particularly useful in the preparation of antibacterial 1-alkyl-1,4-dihydro-4-oxo-7-pyridinyl-3-quinolinecarboxylic acids.

9 Claims, No Drawings

2-AMINO-4-(4-PYRIDINYL)BENZOIC ACIDS

FIELD OF THE INVENTION

This invention relates to 2-amino-4-(4-pyridinyl)benzoic acids, a process for preparing them, and processes for preparing derivatives thereof.

BACKGROUND

As disclosed in Sterling Drug's U.S. Pat. Nos. 3,753,993 (Lesher et al.), 3,907,808 (Lesher and Carabateas), and 4,118,557 (Lesher), it is known that antibacterial 1-alkyl-1,4-dihydro-4-oxo-7-pyridinyl-3-quinolinecarboxylic acids can be prepared from 4-(3-aminophenyl)pyridine. It is also known that this route to the bactericides, as disclosed, is less economical than might be desired.

From Mitscher et al., "Quinoline Antimicrobial Agents. 1. Versatile New Synthesis of 1-Alkyl-1,4-dihydro-4-oxo-3-quinolinecarboxylic Acids," *Journal of Medicinal Chemistry*, 1978, Vol. 21, No. 5, pp. 485-489, It is also known that antimicrobial agents related to the aforementioned bactericides can be prepared from the appropriate isatoic anhydrides.

It would be desirable to be able to prepare the antibacterial agents of Lesher, Lesher et al, and Lesher and Carabateas by a route similar to that employed by Mitscher et al. However, although, as indicated in copending application Ser. No. 511,887, filed July 8, 1983, in the name of Thomas J. Walter (Walter), this route to the antibacterial agents can be employed when 4-(4-alkyl-3-nitrophenyl)pyridines are utilized, it has previously been found difficult to convert the 4-(4-alkyl-3-nitrophenyl)pyridines to the acids, salts, or esters required for conversion to suitable isatoic anhydrides. Thus, a satisfactory method of synthesizing a material capable of being converted into a suitable isatoic anhydride has not previously been proposed.

SUMMARY OF INVENTION

An object of this invention is to provide 2-amino-4-(4-pyridinyl)benzoic acids which are convertible to 1-alkyl-1,4-dihydro-4-oxo-7-pyridinyl-3-quinolinecarboxylic acids via isatoic anhydrides.

Another object is to provide a process for preparing the 2-amino-4-(4-pyridinyl)benzoic acids.

A further object is to provide a process for preparing derivatives of the 2-amino-4-(4-pyridinyl)benzoic acids.

These and other objects are attained by treating a 4-(4-alkyl-3-nitrophenyl)pyridine with an alcoholic base to produce a 2-amino-4-(4-pyridinyl)benzoic acid and, when appropriate, converting the acid to a desired derivative thereof.

DETAILED DESCRIPTION 4-(4-Alkyl-3-nitrophenyl)pyridines utilizable in the practice of the invention are compounds corresponding to the formula:

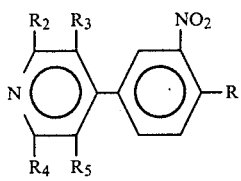

wherein R is alkyl, e.g., a methyl or other alkyl group containing 1-6 carbons, and $R_2$, $R_3$, $R_4$, and $R_5$ are independently selected from hydrogen and innocuous substituents, such as substituted (e.g., halogenated) and unsubstituted aryl and aryloxy groups, halo, etc. These compounds are preferably prepared by the process taught in Walter, the teachings of which are incorporated herein by reference. As indicated in Walter, the preferred 4-(4-alkyl-3-nitrophenyl)pyridine, when the aforementioned bactericides are to be prepared, is 4-(4-methyl-3-nitrophenyl)pyridine.

The base employed in the treatment of the 4-(4-alkyl-3-nitrophenyl)pyridine may be any suitable base, generally an alkali metal hydroxide, such as sodium or potassium hydroxide. The alcoholic treating agent may be any alkanol containing about 1-6 carbons but is preferably methanol.

In the practice of the invention, the treatment of the 4-(4-alkyl-3-nitrophenyl)pyridine with the alcoholic base is generally conducted at reflux temperatures for a time sufficient to achieve the desired conversion, e.g. about 9 hours.

The 2-amino-4-(4-pyridinyl)benzoic acids formed in the process of the invention are compounds corresponding to the formula:

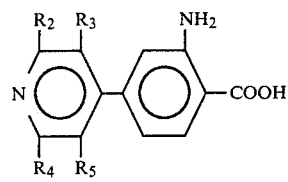

wherein $R_2$, $R_3$, $R_4$, and $R_5$ have the same definitions as given above. When the aforementioned bactericides are to be prepared, the preferred product is 2-amino-4-(4-pyridinyl)benzoic acid. These compounds are useful in the synthesis of a variety of materials but are particularly useful as intermediates in the production of the antibacterial 1-alkyl-1,4-dihydro-4-oxo-7-pyridinyl-3-quinolinecarboxylic acids of Lesher, Lesher et al., and Lesher and Carabateas, i.e., compounds corresponding to the formula:

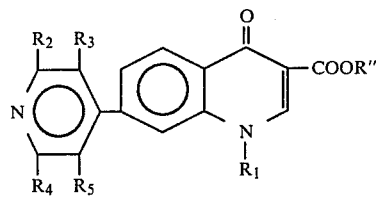

wherein R" is hydrogen or alkyl, $R_1$ is alkyl, haloalkyl, or hydroxyalkyl, and $R_2$, $R_3$, $R_4$, and $R_5$ have the same definitions as given above—any aliphatic groups generally containing 1-6 carbons.

The synthesis of these bactericides from the 2-amino-4-(4-pyridinyl)benzoic acids may be accomplished by conventional techniques, e.g.:

(1) 2-amino-4-(4-pyridinyl)benzoic acid can be converted to 4-(4-pyridinyl)isatoic anhydride, e.g., by reaction with phosgene, (2) the 4-(4-pyridinyl)isatoic anhydride can be N-alkylated, generally N-ethylated, by reaction with a suitable alkylating agent, e.g., the appropriate organic halide, (3) the resultant N-alkyl-4-(4-pyridinyl)isatoic anhydride may be reacted with an alkali metal salt of an alkyl (e.g., ethyl) formyl acetate to form an alkyl 1-alkyl-1,4-dihydro-4-oxo-7-pyridinyl-3-quinolinecarboxylate, e.g., ethyl 1-ethyl-1,4-dihydro-4-oxo-7-pyridinyl-3-quinolinecarboxylate, and (4) the alkyl 1-alkyl-1,4-dihydro-4-oxo-7-pyridinyl-3-quinolinecarboxylate may then be hydrolyzed to the corresponding 1-alkyl-1,4-dihydro-4-oxo-7-pyridinyl-3-quinolinecarboxylic acid.

The following example is given to illustrate the invention and is not intended as a limitation thereof.

EXAMPLE

A suitable reaction vessel was charged with 1.5 g of 4-(3-nitro-4-methylphenyl)pyridine and 20 ml of 30% methanolic KOH, and the reaction mixture was refluxed for about 9 hours. Excess methanol was evaporated from the crude reaction mixture, and the residue was taken in water and extracted with methylene chloride to remove unreacted starting material. Then the aqueous layer was carefully neutralized with acetic acid to a pH of about 6. The solid material thrown out of solution was filtered and washed to give about 300 mg of a brown material, which analysis showed to be crude 2-amino-4-(4-pyridinyl)benzoic acid.

It is obvious that many variations may be made in the products and processes set forth above without departing from the spirit and scope of this invention.

I claim:

1. A compound corresponding to the formula:

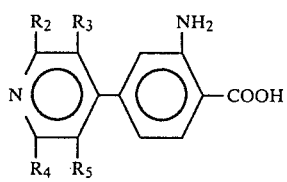

wherein $R_2$, $R_3$, $R_4$, and $R_5$ are independently selected from hydrogen, halo, and halogenated and unhalogenated phenyl and phenoxy substituents.

2. 2-Amino-4-(4-pyridinyl)benzoic acid.

3. A process which comprises heating a reaction mixture consisting essentially of a 4-(4-methyl-3-nitrophenyl)pyridine and an alcoholic base at reflux temperatures so as to produce a 2-amino-4-(4-pyridinyl)benzoic acid.

4. The process of claim 3 wherein the 4-(4-methyl-3-nitrophenyl)pyridine is 4-(4-methyl-3-nitrophenyl)pyridine.

5. The process of claim 3 wherein the alcohol is methanol.

6. The process of claim 3 wherein the base is potassium hydroxide.

7. The process of claim 3 wherein a reaction mixture consisting essentially of 4-(4-methyl-3-nitrophenyl)pyridine and methanolic potassium hydroxide is heated at reflux temperatures so as to produce 2-amino-4-(4-pyridinyl)benzoic acid.

8. In a process for preparing a 1-alkyl-1,4-dihydro-4-oxo-7-pyridinyl-3-quinolinecarboxylic acid by (a) converting a 2-amino-4-(4-pyridinyl)benzoic acid to a 4-(4-pyridinyl)isatoic anhydride, (b) N-alkylating the 4-(4-pyridinyl)isatoic anhydride, (c) reacting the resultant N-alkyl-4-(4-pyridinyl)isatoic anhydride with an alkali metal salt of an alkyl formyl acetate to form an alkyl 1-alkyl-1,4-dihydro-4-oxo-7-pyridinyl-3-quinolinecarboxylate, and (d) hydrolyzing the carboxylate, the improvement which comprises preparing the 2-amino-4-(4-pyridinyl)benzoic acid by heating a reaction mixture consisting essentially of a 4-(4-methyl-3-nitrophenyl)pyridine and an alcoholic base at reflux temperatures.

9. The process of claim 8 wherein the 4-(4-methyl-3-nitrophenyl)pyridine is 4-(4-methyl-3-nitrophenyl)pyridine, the N-alkyl-4-(4-pyridinyl)isatoic anhydride is N-ethyl-4-(4-pyridinyl)isatoic anhydride, and the alkali metal salt of an alkyl formyl acetate is the sodium or potassium salt of ethyl formyl acetate.

* * * * *